United States Patent
Nakamura

(10) Patent No.: US 7,229,435 B2
(45) Date of Patent: Jun. 12, 2007

(54) OPHTHALMIC LASER TREATMENT APPARATUS

(75) Inventor: Hirokazu Nakamura, Nishio (JP)

(73) Assignee: Nidek Co., Ltd., Gamagori (JP)

( * ) Notice: Subject to any disclaimer, the term of this patent is extended or adjusted under 35 U.S.C. 154(b) by 0 days.

(21) Appl. No.: 10/128,461

(22) Filed: Apr. 24, 2002

(65) Prior Publication Data

US 2002/0165525 A1 Nov. 7, 2002

(30) Foreign Application Priority Data

May 1, 2001 (JP) ............................. 2001-134567

(51) Int. Cl.
*A61B 18/18* (2006.01)

(52) U.S. Cl. .................. 606/4; 606/3; 606/11; 606/14; 607/89

(58) Field of Classification Search .................... 606/4, 606/6, 13; 607/88–90
See application file for complete search history.

(56) References Cited

U.S. PATENT DOCUMENTS

| | | | |
|---|---|---|---|
| 5,151,909 A | * | 9/1992 | Davenport et al. ........... 606/12 |
| 5,272,301 A | * | 12/1993 | Finger ........................ 607/116 |
| 5,461,692 A | * | 10/1995 | Nagel ........................... 385/27 |
| 6,096,028 A | * | 8/2000 | Bahmanyar et al. ............ 606/4 |
| 6,542,524 B2 | * | 4/2003 | Miyake ........................ 372/23 |
| 2005/0033388 A1 | * | 2/2005 | Brugger et al. ............... 607/89 |

FOREIGN PATENT DOCUMENTS

JP A 9-192140 7/1997

OTHER PUBLICATIONS

Ophthalmic Instruments from Carl Zeiss, "Innovation Photodynamic Therapy The VISULAS 690s", Zeiss Humphrey Systems, 2000.

* cited by examiner

*Primary Examiner*—Charles A. Marmor, II
(74) *Attorney, Agent, or Firm*—Oliff & Berridge, PLC

(57) ABSTRACT

An ophthalmic laser treatment apparatus which irradiates a laser beam to a patient's eye to be treated is disclosed. The apparatus includes: a first optical fiber which delivers a first laser beam emitted from a first laser source; a first light delivery optical system which forms an image of an emission end surface of the first optical fiber on the affected part of the eye in a predetermined first spot size being in a range of 50 μm to 1000 μm; a second optical fiber which delivers a second laser beam emitted from a second laser source; and a second light delivery optical system which forms an image of an emission end surface of the second optical fiber on the affected part of the eye in a predetermined second spot size in a range of 500 μm to 7000 μm.

15 Claims, 5 Drawing Sheets

OPHTHALMIC LASER TREATMENT APPARATUS

BACKGROUND OF THE INVENTION

1. Field of the Invention

The present invention relates to an ophthalmic laser treatment apparatus which is used to treat a patient's eye by irradiating the eye with a laser beam.

2. Description of Related Art

Photocoagulation or the like of the tissue of fundus is generally performed as ophthalmic laser treatment. As a recent treatment method for age-related macular degeneration (AMD), attention is being given to Photodynamic Therapy (PDT) and Transpupillary Thermotherapy (TTT).

The PDT is a treatment method to treat choroidal neovascularization by intravenously injecting a photosensitive material (a pharmaceutical drug) having the property of selectively accumulating in atypical tissue such as choroidal neovascularization into a patient's arm, and irradiating an affected part of the fundus with a laser beam with a specific absorption wavelength to the drug, so that the affected part is cured by the active oxygen having cytotoxicity produced by the action of the drug. In the photocoagulation, thermal action spreads from a local point of a focus to an ambient region thereof. This would pose a limit to the treatment for choroidal neovascularization in central fovea or a contiguous region thereto. However, the PDT allows the treatment for choroidal neovascularization without causing damage to visual cells even in the central fovea.

On the other hand, the TTT is a noninvasive thermotherapy utilizing slow-acting atrophy or hypofunction of tissue cells by the heat induced by a laser beam from a laser diode or the like. The histologic fragile structure such as the choroidal neovascularization is of high sensitivity. Applying only a small temperature rise to the structure can necrotize the tissue thereof.

To perform the above photocoagulation, PDT, and TTT, heretofore, a hospital's ophthalmology division or the like needs to have some apparatuses (special purpose apparatuses) each having a delivery unit specifically designed for each type of treatment.

However, preparation of the special purpose apparatuses adapted for respective treatments would cause a problem that a wide space is needed for installation of those apparatuses. In addition, the preparation of the specially designed apparatuses would place a burden in cost on the ophthalmology division or the like.

SUMMARY OF THE INVENTION

The present invention has been made in view of the above circumstances and has an object to overcome the above problems and to provide a laser treatment apparatus capable of performing different types of laser treatments.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided an ophthalmic laser treatment apparatus which irradiates a laser beam to an affected part of a patient's eye to be treated, the apparatus including: a first optical fiber which delivers a first laser beam emitted from a first laser source; a first light delivery optical system which forms an image of an emission end surface of the first optical fiber on the affected part of the eye in a predetermined first spot size being in a range of 50 µm to 1000 µm; a second optical fiber which delivers a second laser beam emitted from a second laser source; and a second light delivery optical system which forms an image of an emission end surface of the second optical fiber on the affected part of the eye in a predetermined second spot size in a range of 500 µm to 7000 µm.

According to another aspect of the present invention, there is provided an ophthalmic laser treatment apparatus which irradiates a laser beam to an affected part of a patient's eye to be treated, the apparatus including: a first laser source; a first optical fiber which delivers a first laser beam emitted from the first laser source; a second laser source; a second optical fiber which delivers a second laser beam emitted from the second laser source; and a light delivery optical system, including a magnification changing optical system, which forms an image of an emission end surface of the first optical fiber on the affected part of the eye in a first spot size which is continuously or stepwise changeable in a range of 50 µm to 1000 µm and forms an image of an emission end surface of the second optical fiber on the affected part of the eye in a second spot size which is continuously or stepwise changeable in a range of 500 µm to 7000 µm.

Furthermore, according to another aspect of the present invention, there is provided an ophthalmic laser treatment apparatus which irradiates a laser beam to an affected part of a patient's eye to be treated, the apparatus including: a first laser source; a second laser source; an optical fiber which delivers a first and a second laser beams emitted from the first and second laser sources respectively; and a light delivery optical system, including a magnification changing optical system, which irradiates the first laser beam delivered through the optical fiber to the affected part of the eye in a first spot size which is continuously or stepwise changeable in a range of 50 µm to 1000 µm and irradiates the second laser beam delivered through the optical fiber to the affected part of the eye in a second spot size which is continuously or stepwise changeable in a range of 500 µm to 7000 µm.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
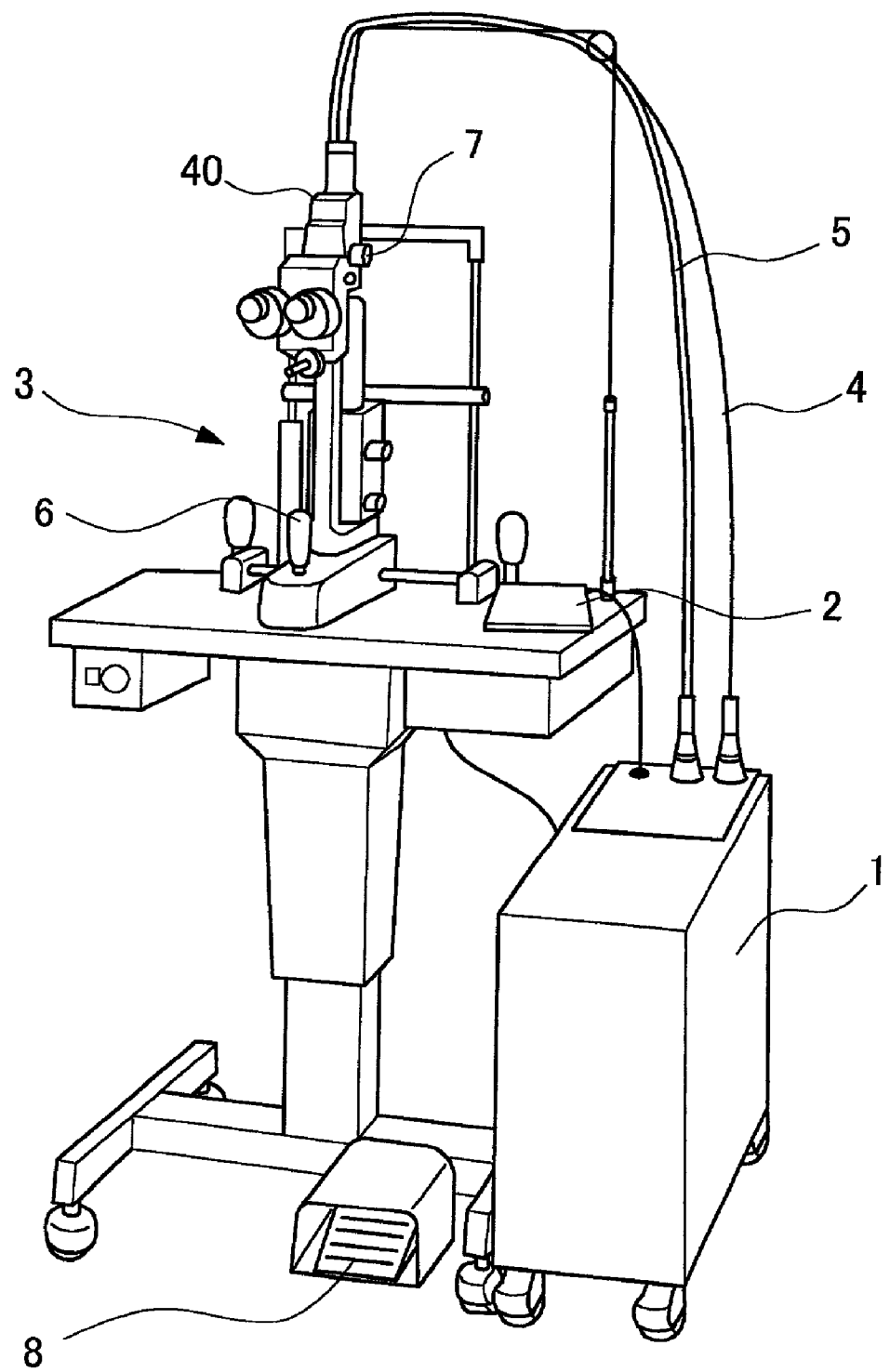
FIG. 1 is a schematic perspective view of a laser treatment apparatus in an embodiment according to the present invention.

A detailed description of preferred embodiments of a laser treatment apparatus embodying the present invention will now be given referring to the accompanying drawings. In the embodiments, an apparatus capable of performing both of photocoagulation and PDT is exemplified. FIG. 1 is a schematic perspective view of the laser treatment apparatus in a first embodiment.

Numeral 1 is a main unit of the laser treatment apparatus, including a laser source unit 70 for photocoagulation and a laser source unit 90 for PDT, both of which will be mentioned later, and other components. Numeral 2 is a control panel used for inputting and setting irradiation conditions of a treatment laser beam and an aiming laser beam, etc. Numeral 3 is a slit lamp delivery including an illumination optical system and an observation optical system. An irradiation unit 40 provided with an irradiation optical system (a light delivery optical system) for irradiating a treatment laser beam to a patient's eye is attached to the slit lamp delivery 3. Numeral 6 is a joystick used for moving the slit lamp delivery 3 in horizontal directions; backward and forward or leftward and rightward. Numeral 7 is a knob used for setting an irradiation spot size of the treatment laser beam. Numeral 8 is a footswitch which generates a trigger signal to start laser irradiation.

Figure 2:
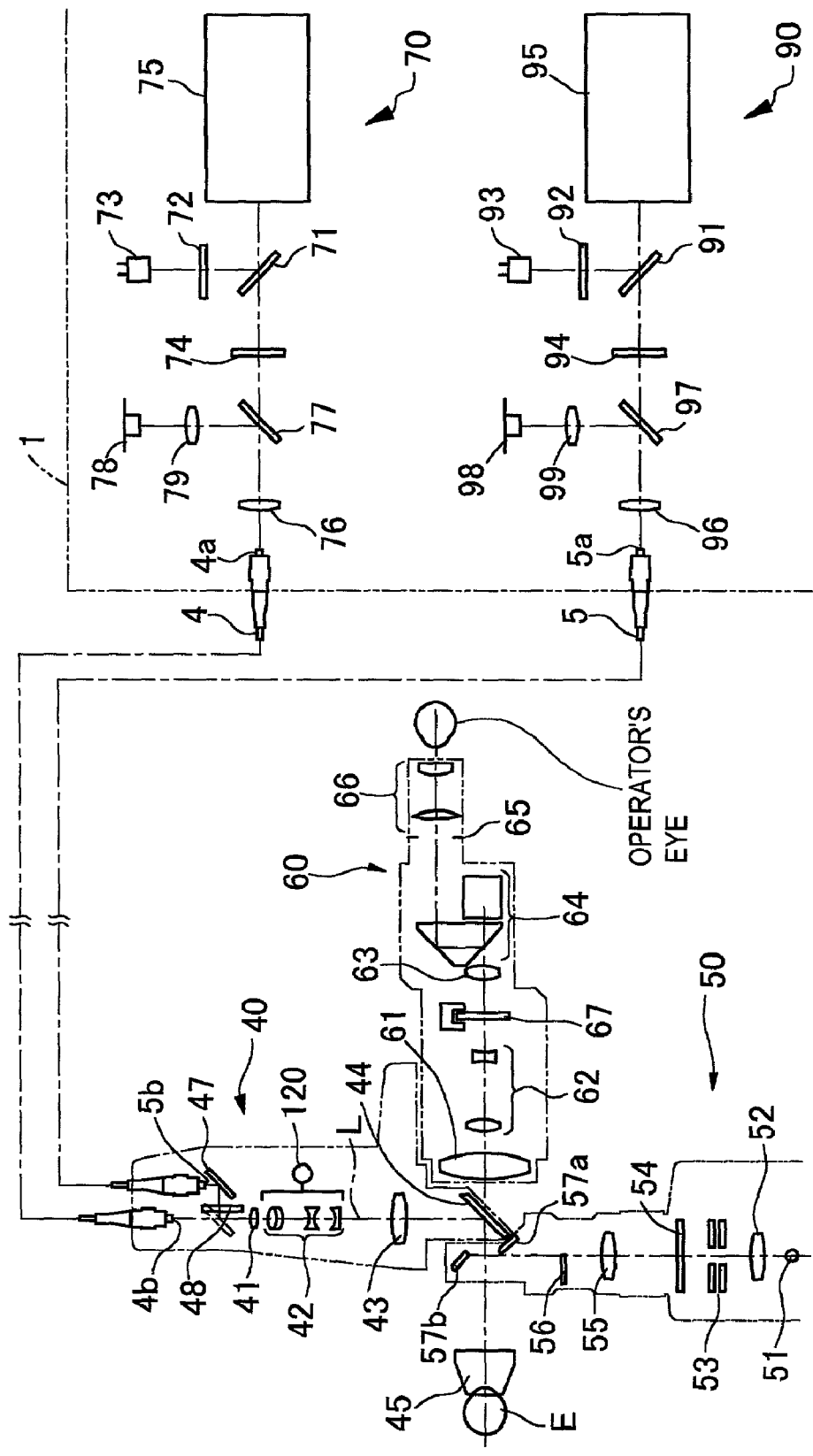
FIG. 2 is a schematic structural view of an optical system of the apparatus.

FIG. 2 is a schematic structural view of optical systems in the apparatus. First explanation is made on an optical system of the laser source unit 70 for photocoagulation disposed in the main unit 1. Numeral 75 is a laser source, used for photocoagulation, which emits a green laser beam having a wavelength of 532 nm as the treatment laser beam for photocoagulation. Numeral 71 is a beam splitter which transmits large part of the treatment beam emitted from the laser source 75 and reflects part of same. The part of the treatment beam reflected by the beam splitter 71 passes through a diffusing plate 72 and enters an output sensor 73. This output sensor 73 detects the output power of the treatment beam emitted from the laser source 75. Numeral 74 is a safety shutter. When the footswitch 8 is pressed down to generate a signal to start irradiation of the treatment beam, the shutter 74 is removed from the optical path by actuation of a shutter driving device 74a shown in FIG. 4, thereby permitting the treatment beam to pass along the optical path. When abnormal conditions are encountered, the shutter 74 is inserted in the optical path to block the treatment beam. Numeral 78 is a laser diode, used as a laser source for aiming, which emits an aiming laser beam having a wavelength of 633 nm. The aiming beam emitted from the laser source 78 passes through a collimator lens 79 and is made coaxial with the treatment beam by a dichroic mirror 77. Numeral 76 is a condensing lens which concentrates each beam on an incident end surface 4a of an optical fiber 4.

Each beam is delivered through the optical fiber 4 to the irradiation unit 40. The optical fiber 4 used in the present embodiment has a core diameter of 50 μm.

Next, an optical system of the laser source unit 90 for PDT disposed in the main unit 1 is explained. This unit 90 has substantially the same structure as that of the above mentioned unit 70 and includes a laser source 95 for PDT, which emits a red laser beam having a wavelength of 689 nm as the treatment laser beam for PDT, a beam splitter 91 which transmits large part of the treatment beam and reflects part of same, a diffusing plate 92 and an output sensor 93 which are disposed in a direction of reflection of the treatment beam by the beam splitter 91, a safety shutter 94 which is removed from or inserted in the optical path by a shutter driving device 94 (see FIG. 4), a laser diode 98, used as a laser source for aiming, which emits an aiming laser beam having a wavelength of 633 nm, a collimator lens 99, a dichroic mirror 97 which makes the treatment beam and the aiming beam coaxial with each other, and a condensing lens 96 which concentrates each beam on an incident end surface 5a of an optical fiber 5. The optical fiber 5 used in the present embodiment is of a core diameter of 400 μm which is eight times larger than that of the optical fiber 4 (50 μm).

Emission ends 4b and 5b of the fibers 4 and 5 are individually connected to the upper portion of the irradiation unit 40. In the unit 40, there is provided an irradiation optical system (the light delivery optical system). This optical system includes a collimating lens 41, a zoom lens (a zoom lens group) 42 disposed movable along an optical axis L of the lens 41 to change a spot size of the treatment beams (the aiming beams) an objective lens 43, and a mirror 44 which reflects the treatment beams and the aiming beams.

Each beam having emerged from the fiber 4 is reflected by the mirror 44 toward a patient's eye E, and is irradiated to an affected part of the eye E through a contact lens 45. The emission end surface 4b is placed at a rear focal point of the collimating lens 41. A spot size of each beam to be irradiated to the fundus of the eye E through the contact lens 45 and the irradiation optical system is determined by the zoom lens 42 whereby the image of the emission end surface 4b is successively changed in a zoom range from 1 to 10 times.

Each beam having emerged from the fiber 5 is reflected by a mirror 47 and a movable mirror 48 removably disposed on the optical axis L and then is delivered to the irradiation optical system constructed of the collimating lens 41, the zoom lens 42, the objective lens 43, and the mirror 44. The emission end surface 5b is placed at the rear focal point of the collimating lens 41 through the mirror 47 and the movable mirror 48. The movable mirror 48 is arranged to change its inclination angle with respect to the optical axis L by operation of a switching mechanism 150 provided in the irradiation unit 40.

Figure 3:
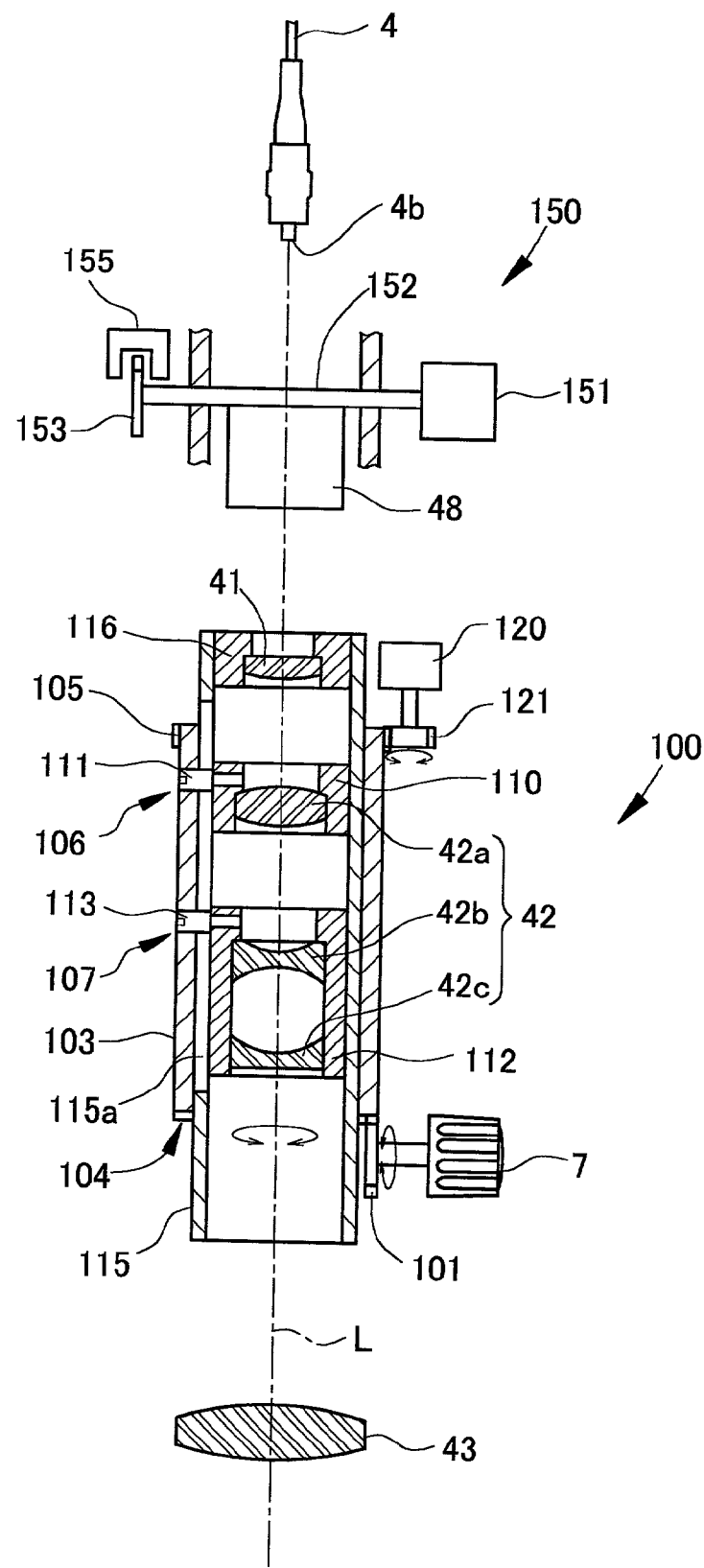
FIG. 3 is a schematic structural view of a spot size changing mechanism and a switching mechanism for light delivery.

FIG. 3 is a schematic structural view of a spot size changing mechanism 100 for changing a spot size by movement of the zoom lens 42 and the switching mechanism 150 for selecting an optical fiber for laser beam delivery.

A cylindrical member 115 fixed to a case of the irradiation unit 40 is provided, on its outer periphery, with a rotatable cylindrical cam 103. A gear 101 is pressure-fitted on a shaft of the knob 7 to be used for setting a spot size and engages with a gear 104 formed in a lower part of the cam 103. A gear 105 formed in an upper part of the cam 103 engages with a gear 121 fixed to a shaft of a potentiometer 120. The zoom lens 42 consists of a convex lens 42a and two concave lenses 42b and 42c. The convex lens 42a is fitted in a holder 110. The concave lenses 42b and 42c are held in a holder 112. Those holders 110 and 112 are vertically movably disposed in the cylindrical member 115. The cylindrical member 115 is formed with a vertical slit 115a in which a pin 111 fixed to the holder 110 and a pin 113 fixed to the holder 112 are engaged. The pins 111 and 113 also engage in cam openings 106 and 107 respectively formed in the periphery of the cam 103. The cam openings 106 and 107 are designed to allow movement of the convex lens 42a and the concave lenses 42b and 42c in a direction of the optical axis L so that a magnification changing optical system capable of zooming by the lens movement is configured.

With this configuration, turning of the knob 7 causes the cam 103 to rotate about the optical axis L, thereby applying pressure to the pins 111 and 113 to vertically move. Thus the convex lens 42a and the concave lenses 42b and 42c are moved vertically in the optical axis L direction to change a spot size. In the case where the treatment beam (the aiming beam) is delivered through the fiber 4, the spot size can successively be changed in a range of 50 µm to 500 µm. In the case where the treatment beam (the aiming beam) is delivered through the fiber 5, on the other hand, the spot size can successively be changed in a range of 400 µm to 4000 µm. The collimating lens 41 is fixedly held in the cylindrical member 115 by means of a holder 116.

It is preferable that the spot size at the photocoagulation is changeable in a range of 50 µm to 1000 µm, at least 100 µm to 500 µm. The spot size at the PDT (TTT) is, on the other hand, preferably changeable in a range of 500 µm to 7000 µm, at least 2000 µm to 3000 µm. The magnification changing optical system may be arranged to stepwise change magnifications of the spot size.

The switching mechanism 150 is constructed of a rotational shaft 152 to which the movable mirror 48 is attached and a driving source 151 such as a rotary solenoid, a motor, or the like, for rotating the rotational shaft 152 about its axis. When the driving source 151 is actuated, the movable mirror 48 is rotated about the shaft 152, thus being inserted in or removed from the optical axis L. A light blocking plate 153 is fixed to an end of the shaft 152. This light blocking plate 153 is detected by a photosensor 155 to detect whether the movable mirror 48 lies on the optical axis L, in other words, which of the treatment beam (the aiming beam) emerging from the fiber 4 and the treatment beam (the aiming beam) emerging from the fiber 5 is allowed to be delivered to the irradiation optical system.

In FIG. 2, numeral 50 is an illumination optical system for projecting slit illumination light on the eye E. This system 50 includes an illumination light source 51, a condensing lens 52, a slit-plate 53, a filter 54, a projection lens 55, a semicircular correcting lens 56, splitting mirrors 57a and 57b, and others. Numeral 60 is an observation optical system including an objective lens 61, a magnification changing optical system 62, an image forming lens 63, an erecting prism group 64, a field diaphragm 65, an eyepiece lens 66, a protection filter 67, and others. Two sets of the components 62 to 67 are disposed one in each of right and left optical paths of the observation optical system 60.

Figure 4:
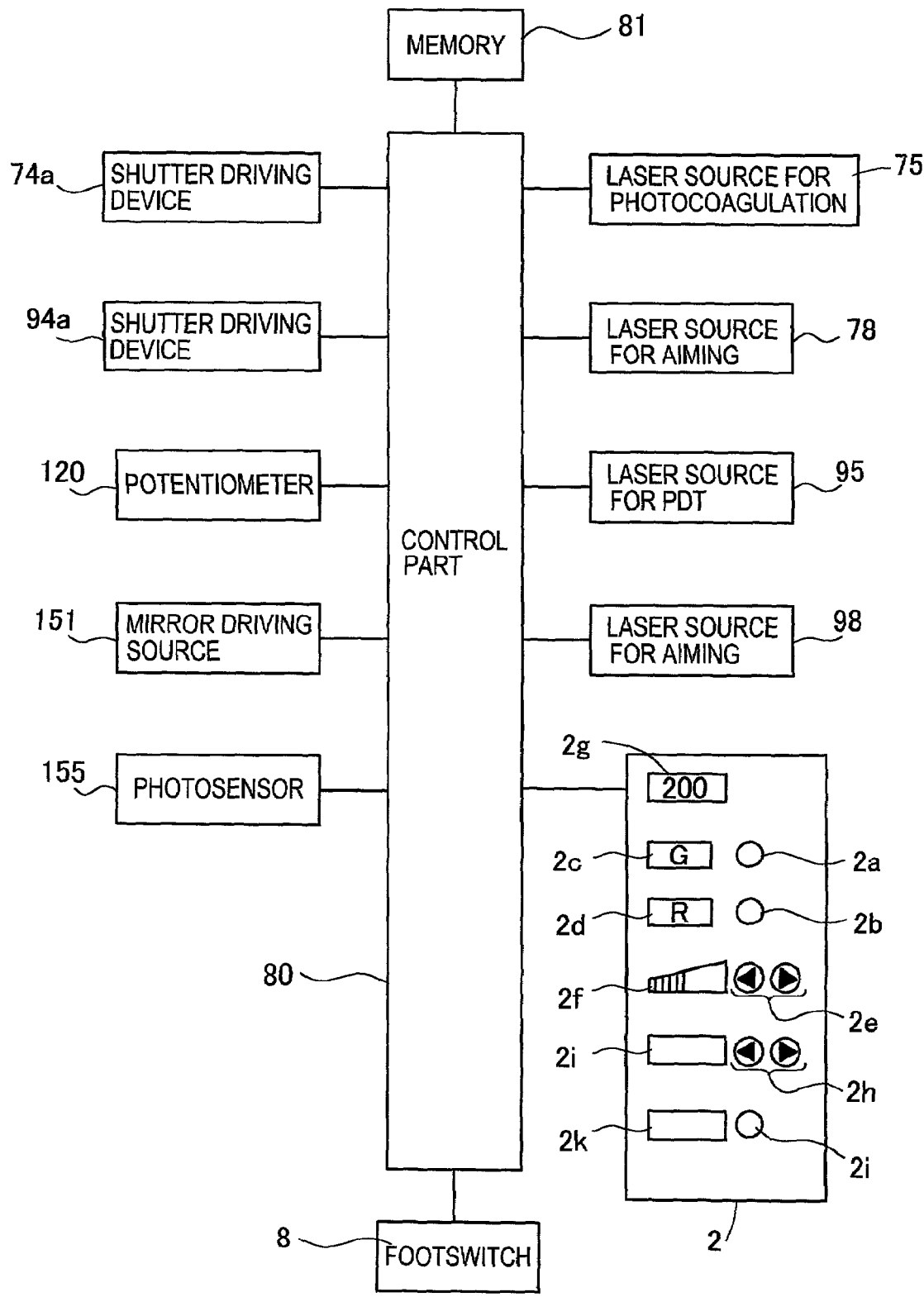
FIG. 4 is a block diagram of a control system of the apparatus.

The operation of the apparatus having the above structure is explained with reference to a schematic block diagram of a control system of the apparatus shown in FIG. 4.

An operator first selects one of a photocoagulation mode and a PDT mode by operation of a photocoagulation mode switch 2a or a PDT mode switch 2b provided on the control panel 2. When the photocoagulation mode is selected by turn-on of the switch 2a, a green indicator 2c lights up and the laser source unit 70 is put in an operable state. This mode selection signal generated upon turn-on of the switch 2a serves as a command signal to move (swing) the movable mirror 48. Upon turn-on of the switch 2a, therefore, the movable mirror 48 is moved (swung) changing its inclination angle to a withdrawn position out of the optical axis L, allowing the treatment beam (the aiming beam) emerging from the fiber 4 to be guided to the irradiation optical system. At this time, the sensor 155 detects whether or not the movable mirror 48 lies on the optical axis L. If the mirror 48 is on the optical axis L, not withdrawn there from, an indicator 2g is caused to indicate an error message.

It is to be noted that the movement of the movable mirror 48 may be manually performed by the use of a knob or the like. In this case, a detection signal from the sensor 155 may be used as a mode switching (selecting) signal. The switching between the fibers 4 and 5 (i.e. the switching between the photocoagulation mode and the PDT mode) may be implemented by simply changing the fiber to be connected to the upper part of the irradiation unit 40. In this case, a sensor for detecting which of the fibers is in connection to the unit 40 is provided to use a detection signal thereof as a mode switching (selecting) signal.

The operator observes the fundus of the eye E through the observation optical system 60, the fundus being illuminated by illumination light from the illumination optical system 50. The operator turns on the laser source 78 with an aiming switch 2e. The aiming beam is thus delivered through the fiber 4 to the irradiation optical system, irradiating the fundus. While observing the aiming beam irradiated to the fundus, the operator operates the joystick 6 to adjust the irradiation position of the aiming beam to the affected part. Please note that numeral 2f is an indicator for indicating output power of the aiming beam.

The spot size of the treatment beam is set by the turn of the knob 7. The potentiometer 120 is rotated in synchronization with the turn of the knob 7. The output signal from the potentiometer 120 is transmitted to a control part 80. In the case of the photocoagulation mode, the treatment beam is delivered through the fiber 4 having the core diameter of 50 µm at the emission end surface thereof. This information has been stored in advance in a memory 81 of the control part 80. The control part 80 computes a spot size from the mode selecting signal from the switch 2a and the output signal from the potentiometer 120 and causes the indicator 2g on the control panel 2 to display a determined value.

The control part 80 also stores in advance default values of laser irradiation conditions for photocoagulation in a memory 81. Upon selection of the photocoagulation mode with the switch 2a, the control part 80 causes indicators 2i and 2k to display the default values of laser irradiation time and laser output power (irradiation power) respectively read from the memory 81. For the photocoagulation, normally, the spot size is set in a range of 50 µm to 500 µm, the output power is set in a range of 50 mW to 500 mW, and the irradiation time is set in a range of 0.05 to 0.5 sec. The operator may further change the laser irradiation time and laser output power (irradiation power) by operation of corresponding switches 2h and 2j.

Subsequently, the operator presses a READY switch not shown to put the apparatus in a laser irradiation enabled state and then presses the footswitch 8 to irradiate the treatment beam. Upon press of the footswitch 8, the control part 80 drives the laser source 75 and causes the shutter driving device 74a to open the shutter 74 at the same time. The treatment beam emitted from the laser source 75 passes through the fiber 4 into the irradiation unit 40. The treatment beam having emerged from the fiber 4 passes through the collimating lens 41, the zoom lens 42, and the objective lens 43 and is reflected by the mirror 44 toward the eye E. The treatment beam is thus irradiated to the affected part of the eye E through the contact lens 45.

To perform the PDT, on the other hand, the switch 2b is turned on. A red indicator 2d lights up and the laser source unit 90 is put in an operable state. The movable mirror 48 is moved (swung) onto the optical axis L, thereby allowing the treatment beam (the aiming beam) emerging from the fiber 5 to be delivered to the irradiation optical system. At this time, the position of the movable mirror 48 is detected by the sensor 155 in the same manner as in the photocoagulation mode. Upon selection of the PDT mode with the switch 2b, simultaneously, the control part 80 changes the default values of the irradiation condition such as the laser irradiation time, the laser output power, etc. to the default values for PDT stored in the memory 81 and displays those values on the control panel 2. For example, the laser irradiation time for PDT is set at several dozen seconds, which is longer than that for photocoagulation set in a range of 0.05 to 0.5 sec.

Changing those laser irradiation time settings every time the treatment mode is changed would be troublesome. Furthermore, the laser output power is usually set at a lower setting in the PDT than in the photocoagulation. This would cause laser irradiation with excessive laser power if the laser power used in the photocoagulation is used as-is in the PDT.

In the present embodiment, the default values of the irradiation conditions are changed in association with the change of the treatment mode, which can facilitate setting operations of the irradiation conditions with improved operability. It is also possible to prevent the laser output power from being inappropriately set. It is to be noted that each default value is overwritten with the value used in the last treatment. If needing further change of the default values, the operator inputs desired ones with corresponding switches on the control panel 2. The irradiation conditions may be reset by the operator whenever the treatment mode is switched from the photocoagulation mode to the PDT mode. To make sure the reset, the indicators 2i and 2k is controlled to blink in order to prompt the operator to input the irradiation conditions. The maximum set value of the laser output power is different between in the photocoagulation mode and the PDT mode. Thus the control part 80 controls the operation of the laser source according to the selected treatment mode.

While observing the aiming beam irradiated to the fundus, in the same way as in the photocoagulation, the operator operates the joystick 6 to adjust the irradiation position of the aiming beam to the affected part. The operator sets the spot size of the treatment beam by turning the knob 7. In synchronization with the turn of the knob 7, the potentiometer 120 is rotated and an output signal representing thereof is transmitted to the control part 80. The control part 80 computes a spot size from the output signal from the potentiometer 120 and causes the indicator 2g to display a determined value. At this time, the PDT mode having been selected, the control part 80 computes the spot size, from the same signal from the potentiometer 120 as in the photocoagulation mode, as a value eight times as large as the spot size determined in the photocoagulation mode. Thus, the spot size displayed in the indicator 2g is different depending on the core diameter of the emission end surface of the fiber even through the same magnification changing optical system in the irradiation unit 40. Accordingly, the operator can perform laser irradiation while correctly recognizing the current spot size. On press of the footswitch 8, the control part 80 actuates the laser source 95 and drives the shutter driving device 94a to open the shutter 94, thereby allowing the treatment beam emitted from the laser source 95 to irradiate the fundus.

Figure 5:
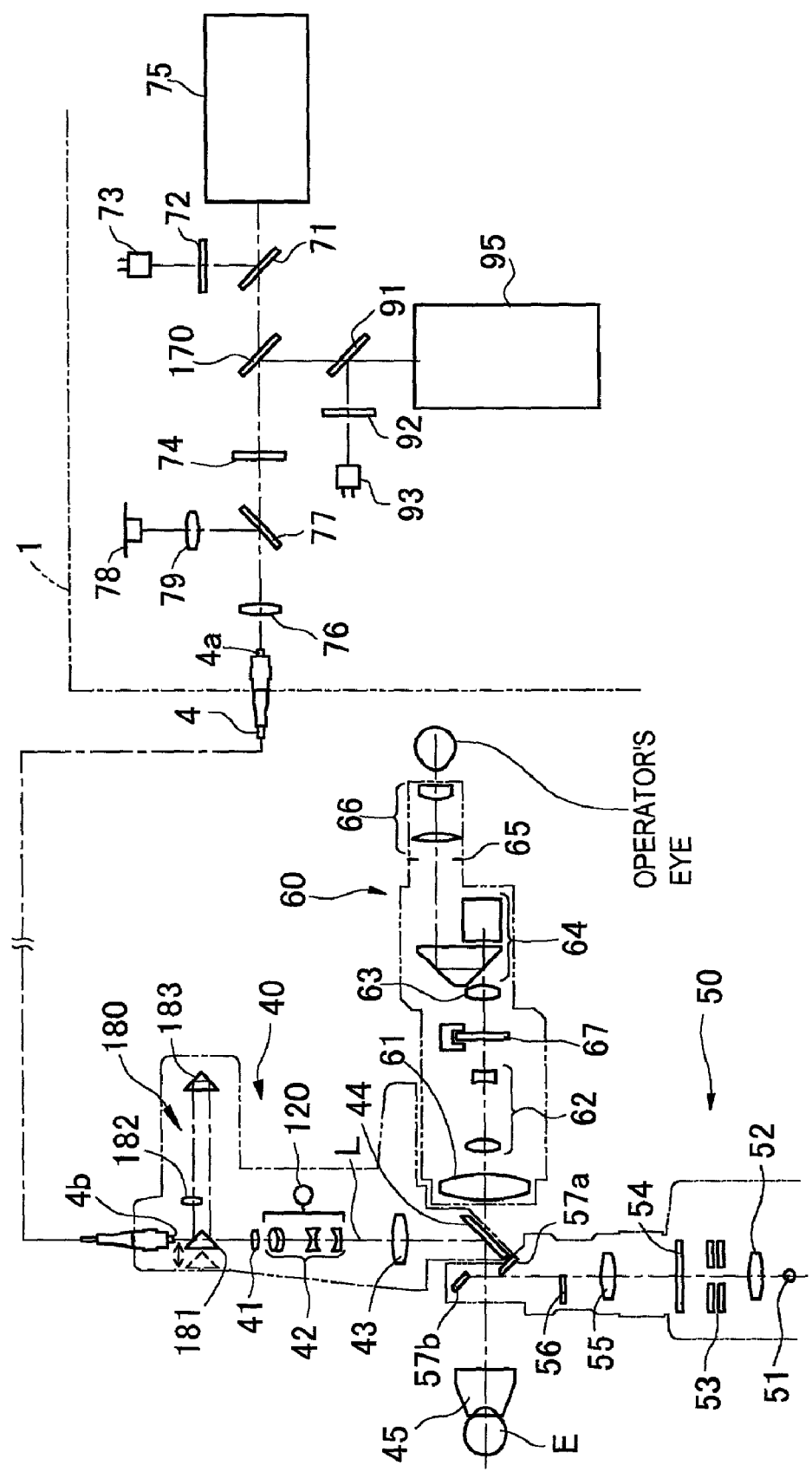
FIG. 5 is a schematic structural view of an optical system of a laser treatment apparatus in a second embodiment.

Next, a second embodiment of the laser treatment apparatus according to the present invention is explained with reference to FIG. 5. FIG. 5 is a schematic structural view of an optical system of a laser treatment apparatus in the second embodiment. In this embodiment, the treatment beam emitted from the laser source 95 for PDT is made coaxial with the treatment beam from the laser source 75 for photocoagulation by a dichroic mirror 170. Both of the treatment beams for photocoagulation and for PDT are delivered to the irradiation unit 40 through the fiber 4 having the core diameter of 50 µm.

In the irradiation unit 40 in the present embodiment, between the emission end surface 4b of the fiber 4 and the collimating lens 41, a relay optical system 180 for changing the magnification of an image of the emission end surface 4b is disposed to be switched between an operative state and an inoperative state. This optical system 180 includes a first prism 181 removably disposed on the optical axis L, and a lens 182 and a second prism 183 placed in an optical bypass. When the first prism 181 is placed on the optical axis L, the treatment beam (the aiming beam) having emerged from the emission end surface 4b is reflected by the first prism 181 toward the lens 182 and the second prism 183 which returns it to the first prism 181, and reflected again by the first prism 181 toward the collimating lens 41. The lens 182 forms an intermediate image of eight times the emission end surface 4b with respect to the collimating lens 41, at a position conjugated with the end surface 4b in the bypass in the relay optical system 180.

Thus, the relay optical system 180 functions as with the change to the diameter of the fiber 5 in the first embodiment. The spot size of the treatment beam can be determined successively in a range of 400 µm to 4000 µm by means of the spot size changing mechanism 100. The switching of the relay optical system 180 between the operative and inoperative states, namely, insertion/removal of the first prism 181 with respect to the optical path may be arranged by a similar mechanism to the switching mechanism 150 in the first embodiment and therefore this arrangement is omitted.

In the second embodiment, similarly, the magnification changing optical system of the irradiation unit 40 can be used in common for both the photocoagulation and the PDT. The same slit lamp delivery unit 3 can be used to selectively, appropriately perform the photocoagulation and the PDT.

The present invention may be embodied in other specific forms without departing from the spirit or essential characteristics thereof. For instance, the above embodiments exemplify the apparatus adaptable to selectively perform the PDT and the photocoagulation. The apparatus of the invention may be arranged to selectively perform the TTT and the photocoagulation. In this case, the laser source 90 for PDT is replaced with a laser source capable of a treatment laser beam having a wavelength needed for TTT, for example, a laser diode which emits a treatment laser beam with a wavelength of 810 nm. In the case of TTT, a large spot size is used as in the case of PDT. It is usually determined in a range of 1000 µm to 3000 µm. The irradiation time is also set longer at about 60 seconds. The laser output power is also set lower than that in the photocoagulation. In this manner, the irradiation conditions set for TTT are similar to those for PDT, so that the laser source 90 for PDT may be used as the laser source for TTT.

As explained above, according to the present invention, a single apparatus allows appropriate execution of different types of laser treatments such as the photocoagulation, PDT, and TTT.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic laser treatment apparatus which irradiates a laser beam to an affected part of a patient's eye to be treated, the apparatus including:

a treatment mode selection switch which is used for selecting a treatment mode between a photocoagulation mode and at least one of a photodynamic therapy (PDT) mode and a transpupillary thermotherapy (TTT) mode;

irradiation condition setting means for automatically setting a default value of an irradiation condition of the laser beam or setting a display to prompt input of a value of the irradiation condition based on the selected treatment mode, the default value being overwritten with the value used in a last treatment a first laser source which emits a first laser beam for photocoagulation;

a first optical fiber which delivers the first laser beam emitted from the first laser source, wherein the first optical fiber has a first core diameter;

a first light delivery optical system which irradiates the first laser beam delivered through the first optical fiber to the affected part and forms an image of an emission end surface of the first optical fiber on the affected part in a first spot size, wherein the first light delivery optical system includes a magnification changing optical system which changes the first spot size in a range of 50 μm to 1000 μm;

a second laser source which emits a second laser beam for at least one of photodynamic therapy (PDT) and transpupillary thermotherapy (TTT), wherein the second laser source is independent from the first laser source;

a second optical fiber which delivers the second laser beam emitted from the second laser source, wherein the second optical fiber has a second core diameter larger than the first core diameter of the first optical fiber; and a second light delivery optical system which irradiates the second laser beam delivered through the second optical fiber to the affected part and forms an image of an emission end surface of the second optical fiber on the affected part in a second spot size, wherein the second light delivery optical system includes the magnification changing optical system, common to the first light delivery optical system, which changes the second spot size in a range of 500 μm to 7000 μm.

2. The ophthalmic laser treatment apparatus according to claim 1 further including:

input means which is used for inputting information on magnification of the magnification changing optical system;

computation means which determines one of the first and second spot sizes based on the information inputted by means of the input means and a selection result by means of the treatment mode selection switch; and display means for displaying a computation result by the computation means.

3. The ophthalmic laser treatment apparatus according to claim 1, wherein the irradiation condition setting means includes switches which are used for adjusting the set values of the irradiation condition.

4. The ophthalmic laser treatment apparatus according to claim 1 further including:

switching means for switching delivery of the first laser beam delivered through the first optical fiber and delivery of the second laser beam delivered through the second optical fiber into the magnification changing optical system.

5. The ophthalmic laser treatment apparatus according to claim 4 further including:

control means for controlling the first laser source or the second laser source based on the selected treatment mode and the set values of the irradiation condition and controlling the switching means based on the selected treatment mode.

6. An ophthalmic laser treatment apparatus which irradiates a laser beam to an affected part of a patient's eye to be treated, the apparatus including:

a treatment mode selection switch which is used for selecting a treatment mode between a photocoagulation mode and at least one of a photodynamic therapy (PDT) mode and a transpupillary thermotherapy (TTT) mode;

irradiation condition setting means for automatically setting a default value of an irradiation condition of the laser beam or setting a display to prompt input of a value of the irradiation condition based on the selected treatment mode, the default value being overwritten with the value used in a last treatment a first laser source which emits a first laser beam for photocoagulation;

a first optical fiber which delivers the first laser beam emitted from the first laser source, wherein the first optical fiber has a first core diameter;

a second laser source which emits a second laser beam for at least one of photodynamic therapy (PDT) and transpupillary thermotherapy (TTT), wherein the second laser source is independent from the first laser source;

a second optical fiber which delivers the second laser beam emitted from the second laser source, wherein the second optical fiber has a second core diameter larger than the first core diameter of the first optical fiber; and a light delivery optical system, which irradiates the first laser beam delivered through the first optical fiber and the second laser beam delivered through the second optical fiber to the affected part and forms an image of an emission end surface of the first optical fiber on the affected part in a first spot size and forms an image of an emission end surface of the second optical fiber on the affected part in a second spot size, wherein the light delivery optical system includes a magnification changing optical system which changes the first spot size in a range of 50 μm to 1000 μm and changes the second spot size in a range of 500 μm to 7000 μm.

7. The ophthalmic laser treatment apparatus according to claim 6, wherein the light delivery optical system includes an optical member for switching between the first laser beam from the first optical fiber and the second laser beam from the second optical fiber to be delivered to the magnification changing optical system.

8. The ophthalmic laser treatment apparatus according to claim 7 further including a sensor which detects a switching state by the optical member.

9. The ophthalmic laser treatment apparatus according to claim 6, wherein the irradiation condition setting means includes switches which are used for adjusting the set values of the irradiation condition.

10. The ophthalmic laser treatment apparatus according to claim 6 further including:
    switching means for switching delivery of the first laser beam delivered through the first optical fiber and delivery of the second laser beam delivered through the second optical fiber into the light delivery optical system.

11. The ophthalmic laser treatment apparatus according to claim 10 further including:
    control means for controlling the first laser source or the second laser source based on the selected treatment mode and the set values of the irradiation condition and controlling the switching means based on the selected treatment mode.

12. An ophthalmic laser treatment apparatus which irradiates a laser beam to an affected part of a patient's eye to be treated, the apparatus including:
    a treatment mode selection switch which is used for selecting a treatment mode between a photocoagulation mode and at least one of a photodynamic therapy (PDT) mode and a transpupillary thermotherapy (TTT) mode;
    irradiation condition setting means for automatically setting a default value of an irradiation condition of the laser beam or setting a display to prompt input of a value of the irradiation condition based on the selected treatment mode, the default value being overwritten with the value used in a last treatment
    a first laser source which emits a first laser beam for photocoagulation;
    a second laser source which emits a second laser beam for at least one of photodynamic therapy (PDT) and transpupillary thermotherapy (TTT), wherein the second laser source is independent from the first laser source;
    an optical fiber which delivers the first laser beam and the second laser beam emitted from the first and second laser sources respectively; and
    a light delivery optical system, which irradiates the first and second laser beams delivered through the optical fiber to the affected part, wherein the light delivery optical system includes a relay optical system which changes magnification of an image of an emission end surface of the optical fiber and delivers the second laser beam and a magnification changing optical system which changes a first spot size of the first laser beam delivered through the optical fiber in a range of 50 μm to 1000 μm and changes a second spot size of the second laser beam delivered through the optical fiber and the relay optical system in a range of 500 μm to 7000 μm.

13. The ophthalmic laser treatment apparatus according to claim 12, wherein the irradiation condition setting means includes switches which are used for adjusting the set values of the irradiation condition.

14. The ophthalmic laser treatment apparatus according to claim 12 further including:
    switching means for selectively enabling delivery of the second laser beam delivered through the second optical fiber into the relay optical system.

15. The ophthalmic laser treatment apparatus according to claim 14 further including:
    control means for controlling the first laser source or the second laser source based on the selected treatment mode and the set values of the irradiation condition and controlling the switching means based on the selected treatment mode.

* * * * *